(12) United States Patent
Bezwada et al.

(10) Patent No.: US 6,403,655 B1
(45) Date of Patent: *Jun. 11, 2002

(54) METHOD OF PREVENTING ADHESIONS WITH ABSORBABLE POLYOXAESTERS

(75) Inventors: Rao S. Bezwada, Whitehouse Station; Dennis D. Jamiolkowski, Long Valley, both of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/375,724

(22) Filed: Aug. 17, 1999

Related U.S. Application Data

(63) Continuation-in-part of application No. 09/062,881, filed on Apr. 20, 1998, which is a continuation-in-part of application No. 08/964,733, filed on Nov. 5, 1997, now Pat. No. 5,859,150, which is a continuation-in-part of application No. 08/744,289, filed on Nov. 6, 1996, now Pat. No. 5,698,213, which is a continuation-in-part of application No. 08/611,119, filed on Mar. 5, 1996, now Pat. No. 5,607,687, which is a continuation-in-part of application No. 08/554,614, filed on Nov. 6, 1995, now abandoned, which is a continuation-in-part of application No. 08/399,308, filed on Mar. 6, 1995, now Pat. No. 5,464,929.

(51) Int. Cl.[7] .......................... A61K 47/34; C08G 63/12
(52) U.S. Cl. .................... 514/772.7; 525/437; 525/438; 525/408
(58) Field of Search ............................ 424/486, 78.37; 525/301, 361, 437, 445, 509, 511, 408, 438; 514/772.7

(56) References Cited

U.S. PATENT DOCUMENTS

| | | |
|---|---|---|
| 3,057,892 A | 10/1962 | DeGroote |
| 3,997,512 A | 12/1976 | Casey et al. |
| 4,440,922 A | 4/1984 | Barbee et al. |
| 4,510,295 A | 4/1985 | Bezwada et al. |
| 4,535,145 A | 8/1985 | Troxler et al. |
| 4,546,152 A | 10/1985 | Koelmel et al. |
| 4,552,948 A | 11/1985 | Barbee et al. |
| 4,689,424 A | 8/1987 | Shalaby et al. |
| 4,703,069 A | 10/1987 | Kolan et al. |
| 4,730,069 A | 3/1988 | Kolar et al. |
| 4,883,699 A | 11/1989 | Aniuk et al. |
| 4,963,641 A | 10/1990 | Davis |
| 5,017,675 A | 5/1991 | Marten et al. |
| 5,298,618 A | 3/1994 | Speranza et al. |
| 5,349,028 A | 9/1994 | Takahashi et al. |
| 5,442,032 A | 8/1995 | Arnold et al. |
| 5,464,929 A | 11/1995 | Bezwada et al. |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,645,850 A | 7/1997 | Bezwada et al. |
| 5,648,088 A | 7/1997 | Bezwada et al. |
| 5,698,213 A | 12/1997 | Jamiolkowski et al. |
| 5,700,583 A | 12/1997 | Jamiolkowski et al. |
| 5,859,150 A * | 1/1999 | Jamiolkowski et al. |

FOREIGN PATENT DOCUMENTS

| | | |
|---|---|---|
| DE | 1 239 097 | 4/1967 |
| EP | 579 503 A2 | 1/1994 |
| EP | 731 123 | 9/1996 |
| EP | 771 832 A2 | 5/1997 |
| EP | 771 849 A2 | 5/1997 |
| EP | 794 208 | 9/1997 |
| WO | WO 93 15130 | 8/1993 |

OTHER PUBLICATIONS

Sugihara Norihiro, "Production of Condensation Polymer," Abstract of Japan, Jun. 28, 1982.

"Water–Soluble Polyamides," Journal of Polymer Science, 1961, vol. 51, Issue 156.

"Attempts to Prepare Regularly Sequenced Polyamides Containing Oxyethylene and Iminoethylene Units," Die Angewandte Makromoiekulare Chemie 113, 1983, pp. 53–59.

Inventor: Oka Osamu; Applicant: Tomoegawa Paper Co., Ltd., "Polyaniline Derivative And Its Production," Patent Abstracts of Japan, Jun. 14, 1994, Application Date: Dec. 1, 1992.

Patent Abstract of Japan No. 59001532 of Application No. 5710993, Sep. 29, 1993.

* cited by examiner

Primary Examiner—Edward J. Webman

(57) ABSTRACT

The present invention describes a method of preventing adhesion formation between tissues in an animal by placing a sterile polyoxaester adhesion prevention barrier between the tissues of the animal to prevent an adhesion from forming.

7 Claims, No Drawings

METHOD OF PREVENTING ADHESIONS WITH ABSORBABLE POLYOXAESTERS

This patent is a continuation-in-part of U.S. patent application Ser. No. 09/062,881, filed Apr. 20, 1998, now U.S. Pat. No. 6,147,168, which is a continuation-in-part of Ser. No. 08/964,733, filed on Nov. 5, 1997, now U.S. Pat. No. 5,859,150, which is a continuation-in-part of Ser. No. 08/744,289, filed on Nov. 6, 1996, now U.S. Pat. No. 5,698,213, which is a continuation-in-part of Ser. No. 08/611,119, filed Mar. 5, 1996, now U.S. Pat. No. 5,607,687, which is a continuation-in-part of Ser. No. 08/554,614, filed Nov. 6, 1995, now abandoned, which is a continuation-in-part of Ser. No. 08/399,308, filed Mar. 6, 1995, now U.S. Pat. No. 5,464,929 all assigned to Ethicon, Inc.

FIELD OF THE INVENTION

The present invention relates to a method of preventing adhesions with bioabsorbable polymers, copolymers and blends thereof.

BACKGROUND OF THE INVENTION

Since Carothers early work in the 1920s and 1930s, aromatic polyesters particularly poly(ethylene terephthalate) have become the most commercial important polyesters. The usefulness of these polymers is intimately linked to the stiffening action of the p-phenylene group in the polymer chain. The presence of the p-phenylene group in the backbone of the polymer chain leads to high melting points and good mechanical properties especially for fibers, films and some molded products. In fact poly(ethylene terephthalate) has become the polymer of choice for many common consumer products, such as one and two liter soft drink containers.

Several related polyester resins have been described in U.S. Pat. Nos. 4,440,922, 4,552,948 and 4,963,641 which seek to improve upon the properties of poly(ethylene terephthalate) by replacing terephthalic acid with other related dicarboxylic acids which contain phenylene groups. These polymers are generally designed to reduce the gas permeability of aromatic polyesters.

Other aromatic polyesters have also been developed for specialty applications such as radiation stable bioabsorbable materials. U.S. Pat. Nos. 4,510,295, 4,546,152 and 4,689,424 describe radiation sterilizable aromatic polyesters which can be used to make sutures and the like. These polymers, like poly(ethylene terephthalate), have phenylene groups in the backbone of the polymers.

However, less research has been reported on aliphatic polyesters. After Carothers initial work on polyesters, aliphatic polyesters were generally ignored because it was believed that these materials had low melting points and high solubilities. The only aliphatic polyesters that have been extensively studied are polylactones such as polylactide, polyglycolide, poly(p-dioxanone) and polycaprolactone. These aliphatic polylactones have been used primarily for bioabsorbable surgical sutures and surgical devices such as staples. Although polylactones have proven to be useful in many applications they do not meet all the needs of the medical community. For example films of polylactones do not readily transmit water vapor, therefore, are not ideally suited for use as bandages where the transmission of water vapor would be desired.

Recently there has been renewed interest in non-lactone aliphatic polyesters. U.S. Pat. No. 5,349,028 describes the formation of very simple aliphatic polyesters based on the reaction of a diol with a dicarboxylic acid to form prepolymer chains that are then coupled together. These polyesters are being promoted for use in fibers and molded articles because these polyesters are biodegradable after they are buried, such as in a landfill. However, these materials are not disclosed as being suitable for use in surgical devices.

To address the deficiencies in the polymers described in the prior art, we invented a new class of polymers which are disclosed in U.S. Pat. Nos. 5,464,929; 5,595,751; 5,597,579; 5,607,687; 5,618,552; 5,620,698; 5,645,850; 5,648,088; 5,698,213; and 5,700,583 (all of which are hereby incorporated by reference). This new class of polymers is hydrolyzable and suitable for a variety of uses including medical applications. To further broaden the possible uses for these polymers, we are disclosing and claiming herein, copolymers of the polyoxaamides (which includes polyoxaesteramides) and blends thereof with other polymers with modified hydrolysis profiles. These polymers may be used in industrial and consumer applications where biodegradable polymers are desirable, as well as, in medical devices.

SUMMARY OF THE INVENTION

We have discovered a method of preventing adhesion formation between tissues in an animal comprising placing a sterile adhesion prevention barrier between the tissues of the animal where the adhesion is to be prevented wherein the sterile adhesion prevention barriers made from a polymer, copolymer or blends thereof of a polyoxaester copolymer having a first divalent repeating unit of formula IA:

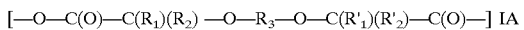

$$[-O-C(O)-C(R_1)(R_2)-O-R_3-O-C(R'_1)(R'_2)-C(O)-]\ \text{IA}$$

and a second repeating unit selected from the group of formulas consisting of:

$$[-O-R_4-]_A,\quad\quad \text{II}$$

$$[-O-R_5-C(O)-]_B,\quad\quad \text{III}$$

$$([-O-R_5-C(O)]_P-O-)_G\quad\quad \text{XI}$$

and combinations thereof, wherein $R_1$, $R'_1$, $R_2$ and $R'_2$ are independently hydrogen or an alkyl group containing 1 to 8 carbon atoms; $R_3$ is an alkylene unit containing from 2 to 12 carbon atoms or is an oxyalkylene group of the following formula:

$$-[(CH_2)_C-O-]_D-(CH_2)_E-\quad\quad \text{IV}$$

wherein C is an integer in the range of from 2 to about 5, D is an integer in the range of from about 0 to about. 2,000, and E is an integer in the range of from about 2 to about 5, except when D is zero, in which case E will be an integer from 2 to 12; $R_4$ is an alkylene unit containing from 2 to 8 carbon atoms ; A is an integer in the range of from 1 to 2,000; $R_5$ is selected from the group consisting of —C($R_6$)($R_7$)—, —(CH$_2$)$_3$—O—, —CH$_2$—CH$_2$—O—CH$_2$—, —CR$_8$H—CH$_2$—, —(CH$_2$)$_5$—, —(CH$_2$)$_F$—O—C(O)— and —(CH$_2$)$_F$—C(O)—CH$_2$—; $R_6$ and $R_7$ are independently hydrogen or an alkyl containing from 1 to 8 carbon atoms; $R_8$ is hydrogen or methyl; F is an integer in the range of from 2 to 6; B is an integer in the range of from 1 to n such that the number average molecular weight of formula III is less than about 200,000, preferably less than about 100,000 and most preferably less than 40,000; P is an integer in the range of from 1 to m such that the number average molecular weight of formula XI is less than about 1,000,000, preferably less than about 200,000 and most preferably less than 40,000; G represents the residue minus from 1 to L hydrogen atoms from the hydroxyl group of an alcohol previously containing from 1 to about 200 hydroxyl groups; and L is an integer from about 1 to about 200.

In another embodiment of the present invention the method of preventing adhesion formation between tissues described above may utilize a barriers made from a polymer, copolymer or blends thereof of a polyoxaester copolymer that additionally contains a third repeating unit of the formula:

$$[-O-C(O)-R_{30}-C(O)-] \quad \text{IB}$$

wherein $R_{30}$ is an alkylene, arylene, arylalkylene, substituted alkylene, substituted arylene and substituted alkylarylene provided that $R_{30}$ cannot be $-[C(R_1)(R_2)]_{1-2}-O-(R_3)-O-[C(R'_1)(R'_2)]_{1-2}-$.

DETAILED DESCRIPTION OF THE INVENTION

The aliphatic polyoxaesters of the present invention are the reaction product of 1) an aliphatic polyoxycarboxylic acid; and 2) at least one of the following compounds: a diol (or polydiol), a lactone (or lactone oligomer), a coupling agent or combination thereof and may optionally contain a dicarboxylic acid. For the purpose of this application aliphatic shall mean an organic compound having a straight, branched, or cyclic arrangement of carbon atoms (i.e. alkanes, olefins, cycloalkanes, cycloolefins and alkynes).

Suitable aliphatic poly-oxycarboxylic acids for use in the present invention are alpha, omega-dicarboxy polyoxy compounds generally have the following formula:

$$HO-C(O)-C(R_1)(R_2)-O-R_3-O-C(R'_1)(R'_2)-C(O)-OH \quad V$$

wherein $R_1$, $R'_1$, $R_2$ and $R'_2$ are independently selected from the group consisting of hydrogen or an alkyl group containing from 1 to 8 carbon atoms and $R_3$ is an alkylene containing from 2 to 12 carbon atoms or is an oxyalkylene group of the following formula:

$$-[(CH_2)_C-O-]_D-(CH_2)_E- \quad IV$$

wherein C is an integer in the range of from about 2 to about 5, D is an integer in the range of-from about 0 to about 2,000 and preferably from 0 to 12, and E is an integer in the range of from about 2 to about 5. These polyoxy aliphatic alpha-omega dicarboxylic acids may be formed by reacting a diol or polydiol with an alpha-halocarboxylic acid such bromoacetic acid or chloroacetic acid under suitable conditions. Oxidation of the ends of a suitable polydiol such as triethylene glycol or tetraethylene glycol is a synthetic route to these acids as well.

Suitable diols or polydiols for use in the present invention are diol or diol repeating units with up to 8 carbon atoms having the formula:

$$H[-(O-R_4-)_A]OH \quad VI$$

wherein $R_4$ is an alkylene unit containing from 2 to 8 methylene units; A is an integer in the range of from 1 to about 2,000 and preferably from 1 to about 1000. Examples of suitable diols include diols selected from the group consisting of 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof. Examples of preferred polydiols include polydiols selected from the group consisting of polyethylene glycol ($H[-O-CH_2-CH_2-]_AOH$) and polypropylene glycol ($H[-O-CH_2-CH(CH_3)-]_AOH$).

Suitable non-dioxycarboxylic acids may be polyfunctional for use in the present invention generally have the following formula:

$$HOOC-R_{30}-COOH \quad VA$$

wherein $R_{30}$ is an alkylene, arylene, arylalkylene, substituted alkylene, substituted arylene and substituted alkylarylene provided that $R_{30}$ cannot be $[-C(R_1)(R_2)]_{1-2}-O-(R_3)-O-[C(R'_1)(R'_2)]_{1-2}-$; and these non-dioxycarboxylic acids may be substituted with heteroatoms or groups. The non-dioxycarboxylic acids of the present invention are generally polycarboxylic acids and more preferably dicarboxylic acids. However, monocarboxylic acids may be used as end caps for the copolymer that are formed. If carboxylic acids are used that have more than two carboxylic acid groups the resulting copolymers may form star shapes or crosslinked matrices depending on the concentration of the carboxylic acids having more than two carboxylic acid groups. Representative unsaturated aliphatic dicarboxylic acids include, but are not limited to, those selected from the group consisting of maleic acid, fumaric acid and combinations thereof. Representative saturated aliphatic dicarboxylic acids include, but are not limited to, those selected from the group consisting of oxalic acid, malonic acid (propanedioic), succinic (butanedioic), glutaric (pentanedioic), adipic (hexadioic), pimelic (heptanedioic), octanedioic, nonanedioic, decanedoic, undecanedioic, dodecanedioic, hendecanedioic, tetradecanedioic, pentadecanedioic, hexadecanedioic, heptadecandioic, octadecanedioic, nonadecanedioic, eicosanedioic acid and combinations thereof. Representative aromatic dicarboxylic acids include, but are not limited to, those selected from the group consisting of phthalic acid, isophthalic acid, terephthalic acid, phenylenediglycolic acid, caboxymethoxybenzoic acid and combinations thereof.

The ratio of non-dioxycarboxylic acid to aliphatic oxydicarboxylic acid should be in the range of from about 1:99 to about 99:1. The rate of hydrolysis can be controlled, in part, by changing the ratio of the non-oxadiacid-based moeties to those of the oxadiacid-based moities. As the concentration of the non-oxadiacid-based moeties increases, the hydrolysis rate will be lower. Besides taking into account the hydrophilic/hydrophobic nature of the reactants, one can also exert control through the steric nature of the alcohol, amine, and amino alcohol groups employed. Thus the hydrolysis rate of an ester based on a secondary alcohol is slower than that of an ester based on a primary alcohol group. The relative concentration of aromatic moieties will effect the hydrolysis rate. Additionally, the presence of aromatic moieties will help resist the loss of properties that may occur during sterilization by gamma irradiation. Higher concentrations of such groups will be better for cobalt sterilizable products.

The polymer produced by reacting the aliphatic dioxycarboxylic acid with the diols discussed above should provide a polymer generally having the formula:

$$[-O-C(O)-C(R_1)(R_2)-O-(R_3)-O-C(R_1)(R_2)-C(O)-(O-R_4)_A-]_N \quad \text{VIIA}$$

wherein $R_1$, $R_2$, $R_3$, $R_4$ and A are as described above; and N is an integer in the range of from about 1 to about. 10,000 and preferably is in the range of from about 10 to about 1,000 and most preferably in the range of from about 50 to about 200.

The copolymer produced by reacting the non-dioxydicarboxylic acid and aliphatic dioxycarboxylic acid with the diols discussed above should provide a copolymer generally having the formula:

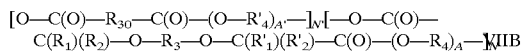

wherein $R_1$, $R_2$, $R'_1$, $R'_2$, $R_3$, $R_4$ and A are as described above; $R'_4$ and A' have the same definitions respectively as $R_4$ and A but vary independently therefrom; N and N' are integers in the range of from about 1 to about 10,000 and preferably is in the range of from about 10 to about. 1,000 and most preferably in the range of from about 50 to about 200.

Suitable lactone monomers that may be used in the present invention generally have the formula:

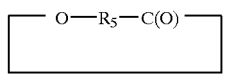

VIII

These lactone monomers may be polymerized to provide copolymers of the following general structures:

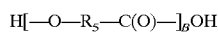   IX

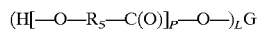   X wherein $R_5$ is selected from the group consisting of —C($R_6$)($R_7$)—, —(CH$_2$)$_3$—O—, —CH$_2$—CH$_2$—O—CH$_2$—, —CR$_8$H—CH$_2$—, —(CH$_2$)$_5$—, —(CH$_2$)$_F$—O—C(O)— and —(CH$_2$)$_F$—C(O)—CH$_2$—; $R_6$ and $R_7$ are independently hydrogen or an alkyl containing from 1 to 8 carbon atoms; $R_8$ is hydrogen or methyl; F is an integer of from about 2 to 6; B is an integer in the range of from 1 to n such that the number average molecular weight of formula IX is less than about 200,000, preferably less than 100,000, and most preferably less than 40,000; P is an integer in the range of from 1 to m such that the number average molecular weight of formula X is less than 1,000,000 about, preferably less than about 200,000 and most preferably less than 40,000; G represents the residue minus from 1 to L hydrogen atoms from the hydroxyl groups of an alcohol previously containing from 1 to about 200 hydroxyl groups; and L is an integer from about 1 to about 200. In one embodiment G will be the residue of a dihydroxy alcohol minus both hydroxyl groups. In another embodiment of the present invention G may be a polymer containing pendent hydroxyl groups (including polysaccharides). Suitable lactone-derived repeating units may be generated from the following monomers include but are not limited to lactone monomers selected from the group consisting of glycolide, d-lactide, 1-lactide, meso-lactide, ε-caprolactone, p-dioxanone, trimethylene carbonate, 1,4-dioxepan-2-one, 1,5-dioxepan-2-one and combinations thereof. The polymer formed by reacting the above described diol (or polydiol) VI and the aliphatic polyoxycarboxylic acid V may also be copolymerized in a condensation polymerization with the lactone polymers IX described above to form a polymer generally of the formula:

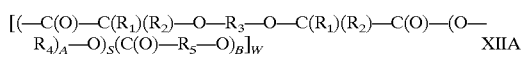

or

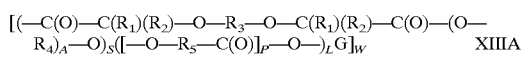

wherein S is an integer in the range of from about 1 to about 10,000 and preferably from about 1 to about 1,000 and W is an integer in the range of from about 1 to about 1,000. These polymers may be made in the form of random copolymers or block copolymers.

The copolymer formed by reacting the above described diol (or polydiol) VI, the nonoxydicarboxylic acids and aliphatic polyoxycarboxylic acid V may also be copolymerized in a condensation polymerization with the lactone polymers IX described above to form a polymer generally of the formula:

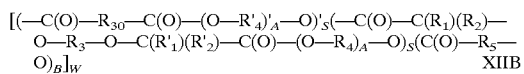

XIIB or

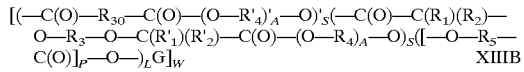

XIIIB wherein S and S' are integers in the range of from about 1 to about 10,000 and preferably from about 1 to about 1,000 and W is an integer in the range of from about 1 to about 1,000. These copolymers may be made in the form of random copolymers or block copolymers.

To the diols, nonoxydicarboxylic acids, aliphatic polyoxycarboxylic acids and lactone monomers described above there may be added a coupling agent selected from the group consisting of polyfunctional (i.e. trifunctional or tetrafunctional) polyols, oxycarboxylic acids, and polybasic carboxylic acids (or acid anhydrides thereof). The addition of the coupling agents causes the branching of long chains, which can impart desirable properties in the molten state to the polyester prepolymer as well as provide desirable properties in the final polymer. Examples of suitable polyfunctional coupling agents include trimethylol propane, glycerin, pentaerythritol, malic acid, citric acid, tartaric acid, trimesic acid, propane tricarboxylic acid, cyclopentane tetracarboxylic anhydride and combinations thereof.

The amount of coupling agent to be added before gelation occurs is a function of the type of coupling. agent used and the polymerization conditions of the polyoxaester or molecular weight of the prepolymer to which it is added. Generally in the range of from about 0.1 to about 10 mole percent of a trifunctional or a. tetrafunctional coupling agent may be added based on the moles of polyoxaester polymers and/or copolymers present or anticipated from the synthesis.

The polymerization of the polyoxaester polymers and copolymer is preferably performed under melt polycondensation conditions in the presence of an organometallic catalyst at elevated temperatures. The organometallic catalyst is preferably a tin-based catalyst e.g. stannous octoate. The catalyst will preferably be present in the mixture at a mole ratio of diol, nonoxycarboxylic acid, aliphatic polyoxycarboxylic; acid and optionally lactone monomer to catalyst will be in the range of from about 15,000 to 80,000/1. The reaction is preferably performed at a temperature no less than about 120° C. under reduced pressure. Higher polymerization temperatures may lead to further increases in the molecular weight of the polymers and copolymer, which may be desirable for numerous applications. The exact reaction conditions chosen will depend on numerous factors, including the properties of the polymers and copolymer desired, the viscosity of the reaction mixture, and the glass transition temperature and softening temperature of the polymer. The preferred reaction conditions of temperature, time and pressure can be readily determined by assessing these and other factors.

Generally, the reaction mixture will be maintained at about 220° C. The polymerization reaction can be allowed to proceed at this temperature until the desired molecular weight and percent conversion is achieved for the polymers and copolymer, which will typically take about 15 minutes to 24 hours. Increasing the reaction temperature generally decreases the reaction time needed to achieve a particular molecular weight.

In another embodiment, polymers and copolymers of polyoxaester can be prepared by forming a polyoxaester prepolymer polymerized under melt polycondensation conditions, then adding at least one lactone monomer or lactone prepolymer. The mixture would then be subjected to the desired conditions of temperature and time to copolymerize the prepolymer with the lactone monomers.

The molecular weight of the prepolymer as well as its composition can be varied depending on the desired characteristic, which the prepolymer is to impart to the copolymer. However, it is preferred that the polyoxaester prepolymers from which the copolymer is prepared have a molecular weight that provides an inherent viscosity between about 0.2 to about 2.0 deciliters per gram (dl/g) as measured in a 0.1 g/dl hexafluoroisopropanol solution at 25° C. Those skilled in the art will recognize that the polyoxaester prepolymers described herein can also be made from mixtures of more than one diol or dioxycarboxylic acid.

One of the beneficial properties of the polyoxaester made by the process of this invention is that the ester linkages are hydrolytically unstable, and therefore the copolymer is bioabsorbable because it readily breaks down into small segments when exposed to moist bodily tissue. By controlling the ratio of oxycarboxylic acid to nonoxycarboxylic acid the hydrolysis rate of the resulting copolymer may be tailored to the desired end product and end use.

These aliphatic polyoxaesters described herein and those described in U.S. Pat. Nos. 5,464,929; 5,595,751; 5,597,579; 5,607,687; 5,618,552; 5,620,698; 5,645,850; 5,648,088; 5,698,213; and 5,700,583 may be blended together with other homopolymers, copolymers and graft copolymers to impart new properties to the material formed by the blend. The other polymers which the aliphatic polyoxaesters may be blended with include but are not limited to homopolymer and copolymer of lactone type polymers with the repeating units described by Formula VIII, aliphatic polyurethanes, polyether polyurethanes, polyester polyurethanes polyethylene copolymers (such as ethylene-vinyl acetate copolymers and ethylene ethyl acrylate copolymers), polyamides, polyvinyl alcohols, poly(ethylene oxide), polypropylene oxide, polyethylene glycol, polypropylene glycol, polytetramethylene oxide, polyvinyl pyrrolidone, polyacrylamide, poly (hydroxy ethyl acrylate), poly(hydroxyethyl methacrylate), absorbable polyoxalates, absorbable polyanhydrides. The copolymers (i.e. containing two or more repeating units) including random, block and segmented copolymers. Suitable lactone-derived repeating units may be generated from the following monomers include but are not limited to lactone monomers selected from the group consisting of glycolide, d-lactide, 1-lactide, meso-lactide, ε-caprolactone, p-dioxanone, trimethylene carbonate, 1,4-dioxepan-2-one, 1,5-dioxepan-2-one and combinations thereof. The blends may contain about 1 weight percent to about 99 weight percent of the aliphatic polyoxaesters.

For some applications it may be desirable to add additional ingredients such as stabilizers, antioxidants radiopacifiers, fillers or the like.

The polymers, copolymers and blends of this invention can be melt processed by numerous methods to prepare a vast array of useful devices. These polymers, copolymers and blends can be injection or compression molded to make implantable medical and surgical devices, especially wound closure devices. The preferred wound closure devices are surgical clips, staples and sutures.

Alternatively, the polymers, copolymers and blends can be extruded to prepare fibers. The filaments thus. produced may be fabricated into sutures or ligatures, attached to surgical needles, packaged, and sterilized by known techniques. The polymers and copolymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for typing up and supporting damaged surface abrasions, particularly major abrasions, or areas where the skin and underlying tissues are damaged or surgically removed.

Additionally, the polymers, copolymers and blends can be processed to form films, felts, foams and gels which, when sterilized, are useful as skin coverings or adhesion prevention devices. Another alternative processing technique for the copolymer and blends of this invention includes solvent casting, particularly for those applications where a drug delivery matrix is desired.

In more detail, the surgical and medical uses of the filaments, films, and molded articles of the present invention include, but are not necessarily limited to:

Knitted products, woven or non-woven, and molded products including:

a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. suture knot clip
j. orthopedic pins, clamps, screws, and plates
k. clips (e.g.,for vena cava)
l. staples
m. hooks, buttons, and snaps
n. bone substitutes (e.g., mandible prosthesis)
o. intrauterine devices (e.g.,spermicidal devices)
p. draining or testing tubes or capillaries
q. surgical instruments
r. vascular implants or supports
s. vertebral discs
t. extracorporeal tubing for kidney and heart-lung machines
u. artificial skin
v. catheters (including, but not limited to, the catheters described in U.S. Pat. No. 4,883,699 which is hereby incorporated by reference)
w. scaffoldings for tissue engineering applications
x. adhesion prevention devices (felts, films, foams and liquids).

In another embodiment, the polyoxaester polymers, copolymers (including prepolymers and suitable crosslinked copolymers and blends) is used to coat a surface of a surgical article to enhance the lubricity of the coated surface (or for drug delivery purposes as described hereinafter). The polymers and copolymers may be applied as a coating using conventional techniques. For example, the polymers and/or copolymers may be solubilized in a dilute solution of a volatile organic solvent, e.g. acetone, methanol, ethyl acetate or toluene, and then the article can be immersed in the solution to coat its surface. Once the surface is coated, the surgical article can be removed from the solution where it can be dried at an elevated temperature until the solvent and any residual reactants are removed.

For use in coating applications the polymers, copolymers and blends should exhibit an inherent viscosity (initial IV in the case of crosslinkable copolymers), as measured in a 0.1 gram per deciliter (g/dl) solution of hexafluoroisopropanol (HFIP), between about 0.05 to about 2.0 dl/g, preferably about 0.10 to about 0.80 dl/g. If the inherent viscosity were less than about 0.05 dl/g (initial IV for crosslinked copolymers), then the copolymer blend may not have the integrity necessary for the preparation of films or coatings for the surfaces of various surgical and medical articles. On the other hand, although it is possible to use copolymer blends with an inherent viscosity greater than about 2.0 dl/g, (initial. IV for crosslinkable polymer or copolymers), it may be exceedingly difficult to do so.

Although it is contemplated that numerous surgical articles (including but not limited to endoscopic instruments) can be coated with the polymers, copolymers and blends of this invention to improve the surface properties of the article, the preferred surgical articles are surgical sutures and needles. The most preferred surgical article is a suture, most preferably attached to a needle. Preferably, the suture is a. synthetic absorbable suture. These sutures are derived, for example, from homopolymers and copolymers of lactone monomers such as glycolide, lactide, $\epsilon$-caprolactone, 1,4-dioxanone, and trimethylene carbonate. The preferred suture is a braided multifilament suture composed of polyglycolide or poly(glycolide-co-lactide).

The amount of coating to be applied on the surface of a braided suture can be readily determined empirically, and will depend on the particular polymer, copolymer or blend and suture chosen. Ideally, the amount of coating applied to the surface of the suture may range from about 0.5 to about 30 percent of the weight of the coated suture, more preferably from about 1.0 to about 20 weight percent, most preferably from 1 to about 5 weight percent. If the amount of coating on the suture were greater than about 30 weight percent, then it may increase the risk that the coating may flake off when the suture is passed through tissue.

Sutures coated with the polymer, copolymers and blends of this invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer, copolymers and blends of this invention.

In another embodiment of the present invention, when the article is a surgical needle, the amount of coating applied to the surface of the article is an amount which creates a layer with a thickness ranging preferably between about 2 to about 20 microns on the needle, more preferably about 4 to about 8 microns. If the amount of coating on the needle were such that the thickness of the coating layer was greater than about 20 microns, or if the thickness was less than about 2 microns, then the. desired performance of the needle as it is passed through tissue may not be achieved.

In yet another embodiment of the present invention, the polymers, copolymers and blends can be used as a pharmaceutical carrier in a drug delivery matrix. To form this matrix the polymers, copolymers and blends would be mixed with a therapeutic agent to form the matrix. The variety of different therapeutic agents which can be used in conjunction with the polyoxaesters of the invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered in any suitable dosage form such as oral, parenteral, a subcutaneously as an implant, vaginally or as a suppository. Matrix formulations containing the copolymers and blends may be formulated by mixing one or more therapeutic agents with the polyoxaester. The therapeutic agent may be present as a liquid, a finely divided solid, or any other appropriate physical form. Typically, but optionally, the matrix will include one or more additives, e.g., nontoxic auxiliary substances such as diluents, carriers, excipients, stabilizers or the like. Other suitable additives may be formulated with the polyoxaester and pharmaceutically active agent or compound, however, if water is to be used, it should advantageously be added immediately before administration.

The amount of therapeutic agent will be dependent upon the particular drug employed and medical condition being treated. Typically, the amount of drug represents about 0.001% to about 70%, more typically about 0.001% to about 50%, most typically about 0.001% to about 20% by weight of the matrix.

The quantity and type of copolymer blend incorporated into the parenteral will vary depending on the release profile desired and the amount of drug employed. The product may contain blends of copolymers having different molecular weights to provide the desired release profile or consistency to a given formulation.

The copolymers and blends, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (over, say 1 to 2,000 hours, preferably 2 to 800 hours) of effective amounts (say, 0.0001 mg/kg/hour to 10. mg/kg/hour) of the drug. This dosage form can be administered as is necessary depending on the subject being treated, the severity of the affliction, the judgment of the prescribing physician, and the like.

Individual formulations of drugs and copolymer or blends may be tested in appropriate in vitro and in vivo models to achieve the desired drug release profiles. For example, a drug could be formulated with a polymer, copolymer or blend and orally administered to an animal. The drug release profile could then be monitored by appropriate means such as, by taking blood samples at specific times and assaying the samples for drug concentration. Following this or similar procedures, those skilled in the art will be able to formulate a variety of formulations.

The polymer, copolymers, and blends of the present invention can be chain extended or crosslinked to affect mechanical properties. Crosslinking may either be chemically or physical. Chemically crosslinked copolymer chains are connected by covalent bonds, which can be formed by the use for trifunctional (or greater) components, reactive groups contained on the copolymers, the addition of crosslinking enhancers and/or irradiation (such as gamma-irradiation). Physical crosslinking on the other hand connects the copolymer chains through crystallization, non-covalent bonds such as van der Waals interactions hydrogen bonding or hydrophobic interactions. In particular, crosslinking can be used to control the water swellability of said invention.

The polymerizable regions are preferably polymerizable by photoinitiation by free radical generation, most preferably in the visible or long wavelength ultraviolet radiation. The preferred polymerizable regions are acrylates, diacrylates, oligoacrylates, methacrylates, dimethacrylates, oligomethoacrylates, or other biologically acceptable photopolymerizable groups.

Other initiation chemistries may be used besides photoinitiation. These include, for example, water and amine initiation schemes with isocyanate or isothiocyanate containing macromers used as the polymerizable regions.

Useful photoinitiators are those which can be used to initiate by free radical generation polymerization of the macromers without cytotoxicity and within a short time frame, minutes at most and most preferably seconds. Preferred dyes as initiators of choice for long wavelength ultraviolet (LWUV) or visible light initiation are ethyl eosin, 2,2-dimethoxy-2-phenyl acetophenone, other acetophenone derivatives, and camphorquinone. Polymerization and/or crosslinking may be initiated among macromers by a light activated free-radical polymerization initiator such as 2,2-dimethoxy-2-phenyl acetophenone, other acetophenone derivatives, and camphorquinone. In other cases, polymerization and/or crosslinking are initiated among macromers by a light-activated free-radical polymerization initiator such as 2,2-dimethoxy-2-phenylacetophenone or a combination of ethyl eosin ($10^{-4}$ to $10^{-2}$M) and triethanol amine (0.001 to 0.1M), for example.

The choice of the photoinitiator is largely dependent on the photopolymerizable regions. Although we do not wish to be limited by scientific theory, it is believed when the macromer includes at least one carbon-carbon double bond, light absorption by the dye can cause the dye to assume a triplet state, the triplet state subsequently reacting with the amine to form a free radical which initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by LWUV light or by laser light of about 514 nm, for example.

Initiation of chain extension or polymerization (and in some cases crosslinking) is accomplished by irradiation with light at a wavelength of between about 200–700 nm, most preferably in the long wavelength ultraviolet range or visible range, 320 nm or higher, most preferably about 514 nm or 365 nm.

There are several photooxidizable and photoreductible dyes that may be used to initiate polymerization. These include acridine dyes, for example, acriblarine; thiazine dyes, for example, thionine; xanthine dyes, for example, rose bengal; and phenazine dyes, for example, methylene blue. These are used with cocatalysis such as amines, for example, triethanolamine; sulphur compounds, for example, $RSO_2R^1$; heterocycles, for example, imidazole; enolates; organometallics; and other compounds, such as N-phenyl glycine. Other initiators include camphorquinones and acetophenone derivatives.

Thermal chain extension polymerization (and optionally crosslinking) initiator systems may also be used. Thermal initiators may be selected to allow polymerization to be initiated at a desired temperature. At times it may be desired to use a high temperature to initiate polymerization such as during a molding process. For many medical uses, it may be desired to use systems that will initiate free radical polymerization at physiological temperatures. Initiator systems include, for example, potassium persulfate, with or without tetramethyl ethylenediamine; benzoylperoxide, with or without triethanolamine; and ammonium persulfate with sodium bisulfite.

The polymer, copolymers (which may be crosslinked) and blends (hereinafter copolymers) can be used for many of the same uses as described heretofor. In addition, copolymers can be used for the prevention of surgical adhesions, tissue adhesives, tissue coatings (sealants) and in tissue engineering.

A preferred application is a method of reducing formation of adhesions after a surgical procedure in a patient. The method includes coating damaged tissue surfaces in a patient with an aqueous solution of a light-sensitive free-radical polymerization initiator and a macromer solution as described above. The coated tissue surfaces are exposed to light sufficient to polymerize the macromer. The light-sensitive free-radical polymerization initiator may be a single compound (e.g., 2,2-dimethoxy-2-phenyl acetophenone) or a combination of a dye and a cocatalyst (e.g., ethyl eosin and triethanol amine).

Additionally, the polymer and copolymers (which are preferably crosslinked) can also be used to form hydrogels that are a three-dimensional network of hydrophilic polymers in which a large amount of water is present. In general the amount of water present in a hydrogel is at least 20 weight percent of the total weight of the dry polymer. The most characteristic property of these hydrogels is that it swells in the presence of water and once swollen, shrinks in the absence of water. The extent of swelling (equilibrium water content) is determined by the nature (mainly the hydrophilicity) of the polymer chains and the crosslinking density.

The kinetics of hydrogel swelling is limited by the diffusion of water through the outer layers of the dried hydrogel. Therefore, while hydrogels swell to a large extent in water, the time it takes to reach equilibrium swelling may be significant depending on the size and shape of the hydrogel. To reduce the amount of time it takes for a hydrogel to reach equilibrium, hydrogel foams may be used. Hydrogels foams may be made by crosslinking polymers in the presence of gas bubbles. The hydrogels foams prepared with macroscopic gas cells will have an open celled structure similar to sponges except that the pore size will generally be an order of magnitude larger.

Hydrogels may be used for many of same uses that have been described for polyoxaesters such as wound dressings materials, since the crosslinked hydrogels are durable, nonantigenic, and permeable to water vapor and metabolites, while securely covering the wound to prevent bacterial infection. Hydrogels may also be used for coatings in general and medical coatings in particular. The hydrogel coatings may provide a smooth slippery surface and prevent bacterial colonization on the surface of the medical instrument. For example hydrogels may be used as coatings on urinary catheter surfaces to improve its biocompatability. Hydrogels may also be used in a variety of applications where the mechanical swelling of the hydrogel is useful such as in catheters as a blend component with a biocompatable elastomer (such as the elastomer described in U.S. Pat. No. 5,468,253 hereby incorporated by reference). Additionally, hydrogels could be used for drug delivery or immobilization of enzyme substrates or cell encapsulization. Other uses for hydrogels have been described in the literature, many of which are discussed in chapter one of *Hydrocels and Biodegradable Polymers for Bioapplications*, published by the Amercian Chemical Society (which is hereby incorporated by reference herein).

Crosslinking to form crosslinked structures can be performed in a variety of ways. For example the polymers may be crosslinked while being synthesized, such as by utilizing multifunctional monomers or oligomers. However, crosslinking at other times is also advantageous. For example crosslinking may be performed during the manufacture of a device such by adding a thermal initiator to the copolymer prior to injection molding a device. Additionally, crosslinking of a polymerizable region with a photoinitiator may be performed during stereolithography to form devices. European Patent Application 93305586.5 describes the process for performing stereolithography (with photopolymerizable materials). As previously discussed photoinitiation may be used in vivo to crosslink the copolymers of the present invention for various wound treatments such as adhesion prevention and wound sealing. Coating may also be applied to devices and crosslinked in situ to form films that will conform to the surface of the device.

In a further embodiment of the present invention the polyoxaesters and polymer blends of the present invention can be used in tissue engineering applications as supports for cells. Appropriate tissue scaffolding structures are known in the art such as the prosthetic articular cartilage described in U.S. Pat. No. 5,306,311, the porous biodegradable scaffolding described in WO 94/25079, and the prevascularized implants described in WO 93/08850 (all hereby incorporated by reference herein). Methods of seeding and/or culturing cells in tissue scaffoldings are also known in the art such as those methods disclosed in EPO 422 209 B1, WO 88/03785, WO 90/12604 and WO 95/33821 (all hereby incorporated by reference herein).

The Examples set forth below are for illustration purposes only, and are not intended to limit the scope of the claimed invention in any way. Numerous additional embodiments within the scope and spirit of the invention will become readily apparent to those skilled in the art.

EXAMPLE 1

Preparation of 3,6-Dioxaoctanedioic acid dimethylester

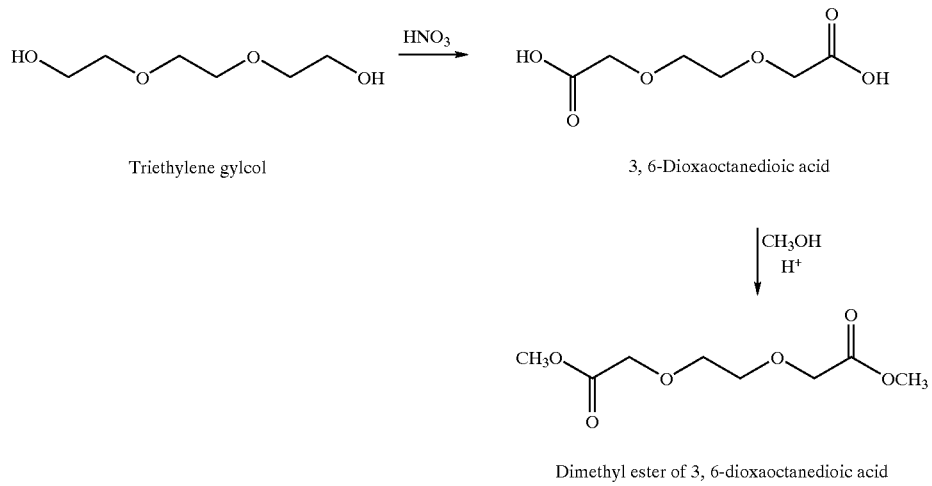

The diacid, 3,6-dioxaoctanedioic acid, was synthesized by oxidation of triethylene glycol. The oxidation was carried out in a 500 milliliter, three-neck round bottom flask equipped with a thermometer, an additional funnel, a gas absorption tube and a magnetic spinbar. The reaction flask was lowered into an oil bath resting upon a magnetic stirrer. To the reaction flask was added 157.3 ml of a 60% nitric acid solution; 37.0 g of triethylene glycol was added to the additional funnel. The contents of the flask were heated to 78–80° C. A test tube containing 0.5 g of glycol and one milliliter of concentrated nitric acid was warmed in a water bath until brown fumes started appearing. The contents were then added to the reaction flask. The mixture was stirred for a few minutes; the glycol was then carefully added. The rate of addition had to be monitored extremely carefully to keep the reaction under control. The addition rate was slow enough so that the temperature of the exothermic reaction mixture was maintained at 78–82° C. After the addition was completed (80 minutes), the temperature of the reaction mixture was maintained at 78–80° C. for an additional hour. While continuing to maintain this temperature range, the excess nitric acid and water was then distilled off under reduced pressure (water suction). The syrupy residue was cooled; some solids appeared. The reaction product had the IR and NMR spectra expected for the dicarboxylic acid; the crude product was used as such for esterification.

Esterification of the crude 3,6-dioxaoctanedioic acid was accomplished as follows: To the reaction flask containing 36 g of the crude diacid, was added 110 ml of. methanol. This was stirred for 3 days at room temperature after which 15 g of sodium bicarbonate was added and stirred overnight. The mixture was filtered to remove solids. To the liquor was added an additional 10 g of sodium bicarbonate; this mixture was stirred overnight. The mixture was again filtered; the liquor was fractionally distilled.

NMR analysis of the esterified product showed a mixture of dimethyl triglycolate (78.4 mole %) and monomethyl-triglycolate (21.6 mole %). No significant condensation of diacid was observed.

EXAMPLE 2

Preparation of polyoxaester from the methyl esters of 3,6-dioxaoctanedioic acid and ethylene glycol

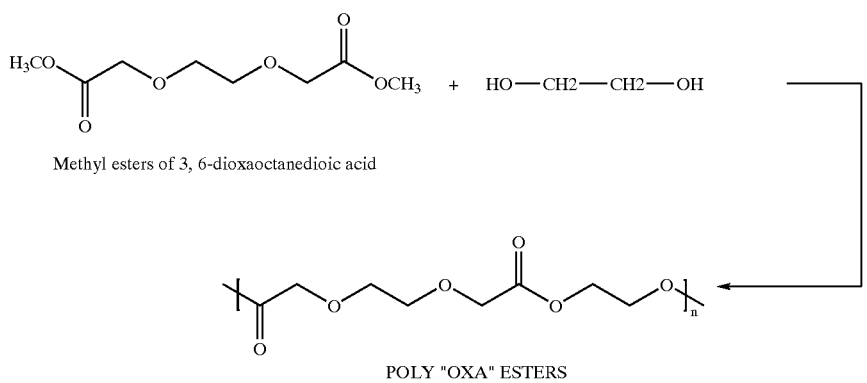

Methyl esters of 3, 6-dioxaoctanedioic acid

POLY "OXA" ESTERS

A flame dried, mechanically stirred, 50-milliliter glass reactor suitable for polycondensation reaction, was charged with 20.62 g (approximately 0.1 mole) of the methyl esters of 3,6-dioxaoctanedioic acid from Example 1, 18.62 g (0.3 mole) of distilled ethylene glycol, and 0.0606 ml of a solution of 0.33M stannous octoate in toluene. After purging the reactor and venting with nitrogen, the temperature was gradually raised over the course of 26 hours to 180° C. A temperature of 180° C. was then maintained for another 20 hours; all during these heating periods under nitrogen at one atmosphere, the methanol formed was collected. The reaction flask was allowed to cool to room temperature; it was then slowly heated under reduced pressure (0.015–1.0 mm) over the course of about 32 hours to 160° C., during which time additional distillates were collected. A temperature of 160° C. was maintained for 4 hours after which a sample, a few grams in size, of the polymer formed was taken. The sample was found to have an inherent viscosity (I.V.) of 0.28 dl/g, as determined in hexaflouroisopropanol (HFIP) at 25° C. at a concentration of 0.1 g/dl. The polymerization was continued under reduced pressure while raising the temperature, in the course of about 16 hours, from 160° C. to 180° C.; a temperature of 180° C. was maintained at for an additional 8 hours, at which time a polymer sample was taken and found to have an I.V. of 0.34 dl/g. The reaction was continued under reduced pressure for another 8 hours at 180° C. The resulting polymer has an inherent viscosity of 0.40 dl/g, as determined in HFIP at 25° C. and at a concentration of 0.1 g/dl.

EXAMPLE 3

Preparation of polyoxaester with 3,6,9-trioxaundecanedioic acid and ethylene glycol A flame dried, mechanically stirred, 250-milliliter glass reactor, suitable for polycondensation reaction, was charged with 44.44 g (0.2 mole) of 3,6,9-trioxaundecanedioic acid, 62.07 g (1.0 mole) of distilled ethylene glycol, and 9.96 milligrams of dibutyltin oxide. After purging the reactor and venting with nitrogen, the contents of the reaction flask were gradually heated

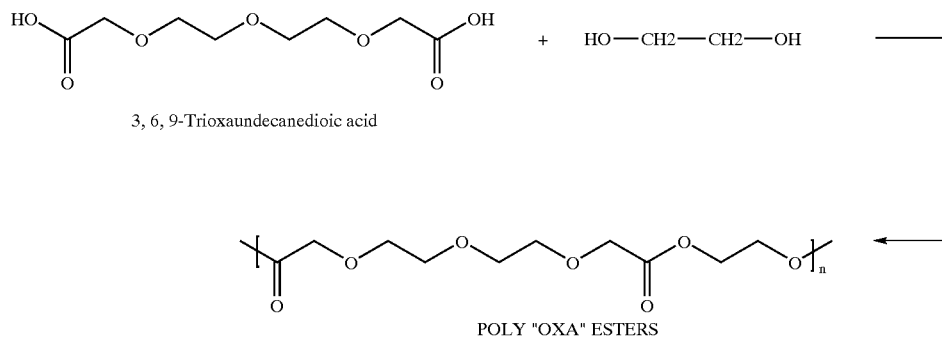

3, 6, 9-Trioxaundecanedioic acid

POLY "OXA" ESTERS under nitrogen at one atmosphere, in the course of about 32 hours, to 180° C., during which time the water formed was collected. The reaction mass was allowed to cool to room temperature. The reaction mass was then heated under reduced pressure (0.015–1.0 mm), gradually increasing the temperature to 180° C. in about 40 hours; during this time additional distillates were collected. The polymerization was continued under reduced pressure while maintaining 180° C. for-an additional 16 hours. The resulting polymer has an inherent viscosity of 0.63 dl/g as determined in HFIP at 25° C. and at a concentration of 0.1 g/dl.

EXAMPLE 4

Preparation of polyoxaester with polyglycol diacid and ethylene glycol

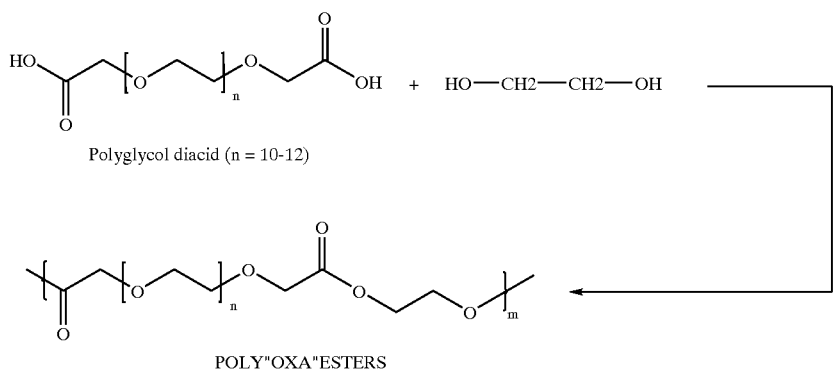

Polyglycol diacid (n = 10-12)

POLY"OXA"ESTERS

A flame dried, mechanically stirred, 500-milliliter glass reactor (suitable for polycondensation reaction) was charged with 123.8 g (0.2 mole) polyglycol diacid (molecular weight about 619), 62.07 g (1.0 mole) of distilled ethylene glycol, and 9.96 milligrams of dibutyltin oxide. After purging the reactor and venting with nitrogen, the contents of the reaction flask was heated under nitrogen at one atmosphere, gradually increasing the temperature to 200° C. in about 32 hours; during this time the water formed was collected. The reaction flask was heated gradually under reduced pressure (0.015–1.0 mm) from room temperature to 140° C. in about 24 hours, during which time additional distillates were collected. A polymer sample of about ten grams was taken at this stage, and found to have an I.V. of 0.14 dl/g in HFIP at 25° C., 0.1 g/dl. The polymerization was continued under reduced pressure while heating from 140° C. to 180° C. in about 8 hours, and then maintained at 180° C. for an additional 8 hours. A polymer sample was again taken and found to have an I.V. of 0.17 dl/g. The reaction temperature was then increased to 190° C. and maintained there under reduced pressure for an additional 8 hours. The resulting polymer has an inherent viscosity of 0.70 dl/g as determined in HFIP at 25° C. and at a concentration of 0.1 g/dl.

EXAMPLE 5

Copolymer of polyoxaester/caprolactone/ trimethylene carbonate at 5/5/5 by weight A flame dried, 50-milliliter, round bottom single-neck flask was charged with 5 grams of the aliquot of the polyoxaester of Example 4 having an I.V. of 0.14 dl/g, 5.0 grams (0.0438 mole) of ε-caprolactone, 5.0 grams (0.0490 mole) of trimethylene carbonate, and 0.0094 milliliters of a 0.33 molar solution of stannous octoate in toluene.

The flask was fitted with a magnetic stirrer bar. The reactor was purged with nitrogen three times before venting with nitrogen. The reaction mixture was heated to 160° C. and maintained at this temperature for about 6 hours. The copolymer was dried under vacuum (0.1 mm Hg) at 80° C. for about 16 hours to remove any unreacted monomer. The copolymer has an inherent viscosity of 0.34 dl/g, as determined in HFIP at 25° C. and at a concentration of 0.1 g/dl. The copolymer is a viscous liquid at room temperature. The mole ratio of polyoxaester/PCL/PTMC was found by NMR analysis to be 47.83/23.73/28.45.

EXAMPLE 6

Copolymer of polyoxaester/caprolactone/glycolide at 6/8.1/0.9 by weight

A flame dried, 25-milliliter, round bottom, single-neck flask was charged with 6 grams of the polyoxaester of Example 4 having an I.V. of 0.17 dl/g., 8.1 grams (0.0731 mole) of ε-caprolactone, 0.9 grams (0.008) mole of glycolide and 0.0080 milliliters of a 0.33 molar stannous octoate solution in toluene. The flask was fitted with a magnetic stirrer bar. The reactor was purged with nitrogen three times before venting with nitrogen. The reaction mixture was heated to 160° C. and maintained at this temperature for about 18 hours. The copolymer has an inherent viscosity of 0.26 dl/g in HFIP at 25° C. and at a concentration of 0.1 g/dl. The copolymer is solid at room temperature. The mole ratio of polyoxaester/PCL/PGA/caprolactone was found by NMR analysis to be 56.54/37.73/3.79/1.94.

EXAMPLE 7

In Vitro Hydrolysis

The polyoxaester of Example 3 was tested for in vitro hydrolysis at both 50° C. and at reflux temperature. A 100 mg sample of the polyoxaester, placed in 100 ml of a phosphate buffer solution (0.2 M in phosphate, pH 7.27), was completely hydrolyzed in about 7 days at 50° C., whereas at reflux it was completely hydrolyzed in about 16 hours.

EXAMPLE 8

In Vitro Hydrolysis

Polyoxaester of Example 2 was tested for in vitro hydrolysis at 50° C. and at reflux temperature. A 100 mg sample of the polyoxaester, placed in a 100 ml buffer solution (pH 7.27), was completely hydrolyzed in about 25 days at 50° C., whereas at reflux it was completely hydrolyzed in about 16 hours.

EXAMPLE 9

Preparation of Polyoxaester Based on Polyglycol Diacid with Polyethylene Glycol

To a flame-dried, 250-ml, 2-neck flask suitable for polycondensation reaction, 15.13 grams of polyglycol diacid (m.w. 619 g/m; 0.02444 mole), 15.0 grams polyethylene glycol (m.w. 600 g/m; Aldrich, 0.025 mole), 3.18 grams ethylene glycol (m.w. 62.07 g/m, 0.0512 mole were charged, and dried over night under high vacuum at room temperature. The next day, 2.5 mg of dibutyl tin oxide (m.w. 248.92) was added. The reaction mass, under nitrogen at one atmosphere, was then gradually heated to 200° C. over a period of 16 hours while collecting the distillate. The reaction flask was allowed to cool to room temperature and the pressure reduced. Now under vacuum, it was gradually heated to 180–200° C., and run at this temperature until the desired molecular weight was obtained. The resulting copolymer has an I.V. of 0.63 dl/g.

EXAMPLE 10

Preparation of Polyoxaester Hydrogel Based on Polyglycol Diacid with Polyethylene Glycol To a flame-dried, 250 ml, 2 neck flask, suitable for polycondensation reaction, 77.34 grams of polyglycol diacid (m.w. 619; 0.125 mole), 63.60 grams of polyethylene glycol (m.w. 600; Aldrich, 0.106 mole), 15.52 grams of ethylene glycol (m.w. 62.07; 0.250 mole), and 2.55 grams of trimethylol propane (m.w. 134.18; 0.019 mole) were charged and dried over night under high vacuum at room temperature. The next day, 12.5 mg of dibutyl tin oxide (m.w 248.92) was charged. The reaction mass, under nitrogen at one atmosphere, was then gradually heated to 190–200° C. over a period of 16 hours while collecting the distillate. The reaction flask was allowed to cool to room temperature and the pressure reduced. Now under vacuum, it was gradually heated to 170° C. and maintained there about 22 hours. The resulting viscous polymer was transferred into a tray for devolatalized in a vacuum oven until a film formed. The resulting film was light brown in color. It swelled in water and was found to disappear in about two weeks.

EXAMPLE 11

Preparation of Copolymers of Polyoxaester Based on Adipic and Polyglycol Diacids with Polyethylene Glycol The following is an example of how a copolymer of polyoxaester could be prepared. To a flame-dried, 250-ml, 2-neck flask suitable for polycondensation reaction, 15.13 grams of polyglycol diacid (m.w. 619 g/m; 0.02444 mole), 0.893 grams of adipic acid (m.w. 146.14 g/m; 0.00611 mole), 15.0 grams polyethylene glycol (m.w. 600 g/m; Aldrich, 0.025 mole), 3.18 grams ethylene glycol (m.w. 62.07 g/m, 0.0512 mole can be charged, and dried over night under high vacuum at room temperature. The next day, a suitable catalyst at a suitable level (i.e. 2.5 mg of dibutyl tin oxide) can be added. The reaction mass, under nitrogen at one atmosphere, can then be gradually heated to 200° C. over a period of 16 hours while collecting the distillate. The reaction flask can be allowed to cool to room temperature and the pressure reduced. Now under vacuum, it can be gradually heated to elevated temperatures (i.e. 180–200° C. or higher) and kept at elevated temperatures until the desired molecular weight is obtained. The ester moieties of the resultant copolymer are approximately 20% adipate in nature. Although the initial charge is rich, on a mole basis, in ethylene glycol, the diol based moieties in the resultant copolymer are much richer in polyethylene glycol-based moieties due to differences in relative volatility.

We claim:

1. An aliphatic polyoxaester having a first repeating unit of the formula:

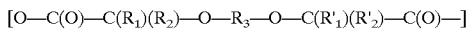

and a second repeating unit selected from the group consisting of formulas

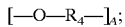

and

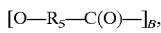

wherein $R_1$, $R'_1$, $R_2$ and $R'_2$ are independently hydrogen or an alkyl group containing 1 to 8 carbon atoms; $R_3$ is an alkylene unit containing from 2 to 12 carbon atoms or is an oxyalkylene group of the following formula:

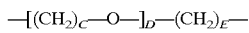      IV wherein C is an integer in the range of from 2 to about 5, D is an integer in the range of from about 0 to about 2,000, and E is an integer in the range of from about 2 to about 5, except when D is zero, in which case E will be an integer from 2 to 12; $R_4$ is an alkylene unit containing from 2 to 8 carbon atoms; A is an integer in the range of from 1 to 2,000; $R_5$ is selected from the group consisting of $—C(R_6)(R_7)—$, $—(CH_2)_3—O—$, $—CH_2—CH_2—O—CH_2—$, $—CR_8H—CH_2—$, $—(CH_2)_5—$, $—(CH_2)_F—O—C(O)—$ and $—(CH_2)_F—C(O)—CH_2—$; $R_6$ and $R_7$ are independently hydrogen or an alkyl containing from 1 to 8 carbon atoms; $R_8$ is hydrogen or methyl; F is an integer in the range of from 2 to 6; B is an integer in the range of from 1 to n such that the number average molecular weight of formula III is less than about 200,000.

2. The aliphatic polyoxaester of claim 1 wherein $R_3$ is an oxyalkylene group.

3. The aliphatic polyoxaester of claim 2 wherein the first repeating unit is derived from a dicarboxylic acid selected from the group consisting of 3,6-dioxaoctanedioic acid, 3,6,9-trioxaundecanedioic acid and combinations thereof.

4. The aliphatic polyoxaester of claim 1 wherein the second repeating unit is derived from a diol selected from the group consisting of 1,2-ethandiol, 1,2-propandiol, 1,3-propandiol and combinations thereof.

5. The aliphatic polyoxaester of claim 1 wherein the second repeating unit is derived from ethylene glycol.

6. The aliphatic polyoxaester of claim 1 wherein the second repeating unit is derived from a lactone selected from the group consisting of glycolide, lactide, ϵ-caprolactone and combinations thereof.

7. The aliphatic polyoxaester of claim 3 wherein the aliphatic polyoxaester has two second repeating units wherein one of the second repeating units is a diol selected from the group consisting of 1,2-ethandiol, 1,2-propandiol, 1,3-propandiol and combinations thereof and the other repeating unit is a lactone selected from the group consisting of glycolide, lactide, ϵ-caprolactone and combinations thereof.

* * * * *